United States Patent [19]

Bock et al.

[11] 4,210,642

[45] Jul. 1, 1980

[54] INSECTICIDAL AND ACARICIDAL COMPOSITIONS

[75] Inventors: Klaus-Detlef Bock, Kelsterbach; Anna Waltersdorfer, Frankfurt am Main, both of Fed. Rep. of Germany

[73] Assignee: Hoechst Aktiengesellschaft, Frankfurt am Main, Fed. Rep. of Germany

[21] Appl. No.: 947,858

[22] Filed: Oct. 2, 1978

[30] Foreign Application Priority Data

Oct. 4, 1977 [DE] Fed. Rep. of Germany ....... 2744540
Nov. 10, 1977 [DE] Fed. Rep. of Germany ....... 2750304

[51] Int. Cl.$^2$ .......................... A01N 9/36; A01N 9/20
[52] U.S. Cl. ..................................... 424/200; 424/304
[58] Field of Search ............................... 424/200, 304

[56] References Cited

U.S. PATENT DOCUMENTS

| 3,686,200 | 8/1972 | Scherer et al. | 424/200 |
| 3,932,629 | 1/1976 | Dawes et al. | 424/200 |
| 3,973,010 | 8/1976 | Dawes et al. | 424/200 |
| 4,031,239 | 6/1977 | Schrider | 424/304 |

FOREIGN PATENT DOCUMENTS 1413491 11/1975 United Kingdom .................... 424/304

*Primary Examiner*—Leonard Schenkman
*Attorney, Agent, or Firm*—Curtis, Morris & Safford

[57] ABSTRACT

Insecticidal and acaricidal compositions which contain a combination of the compound I

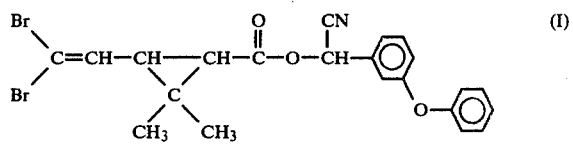

with

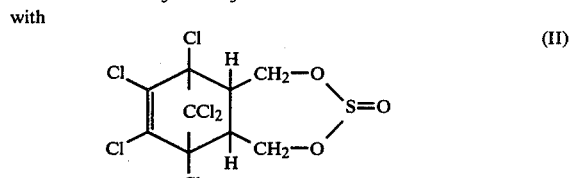

or

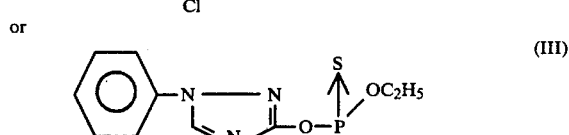

or

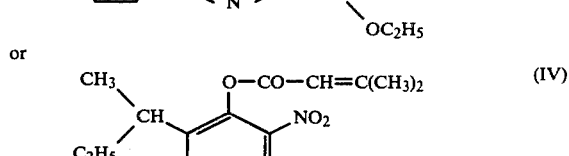

or

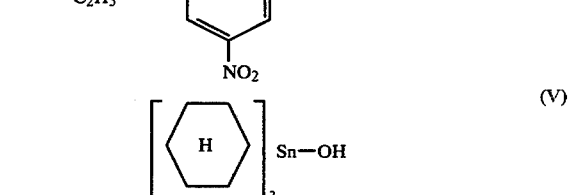

or

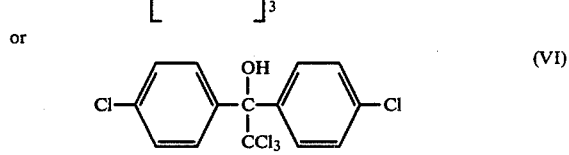

the weight ratio of compound I to compounds II to VI being preferably 10:100 to 50:1, which compositions are distinguished by their synergistic effect against acaridae and the eggs thereof, and against insects.

7 Claims, No Drawings

INSECTICIDAL AND ACARICIDAL COMPOSITIONS

Subject of the present invention are insecticidal and acaricidal compositions containing (S)-α-cyano-m-phenoxybenzoyl-(1 R, 3 R)-3-(2,2-dibromovinyl)-2,2-dimethyl-cyclopropanecarboxylate (common name: Decamethrine) of the formula $$\begin{array}{c} Br \\ \phantom{Br}\diagdown \\ \phantom{Br}\phantom{=}C=CH-CH-CH-\overset{O}{\overset{\|}{C}}-O-\overset{CN}{\overset{|}{CH}}-C_6H_4-O-C_6H_5 \\ Br \diagup \phantom{=========}\diagdown \diagup \\ \phantom{=============}C \\ \phantom{============}\diagup \phantom{=}\diagdown \\ \phantom{===========}CH_3 \phantom{=}CH_3 \end{array}$$ (I)

with (endosulfan structure) (II)
(common name: Endosulfan)

or (triazophos structure) (III)
(common name: Triazophos)

or (binapacryl structure) (IV)
(common name: Binapacryl)

or $[(C_6H_{11})]_3 Sn-OH$ (V)
(common name: Cyhexatin)

or (dicofol structure) (VI)
(common name: Dicofol)

It has been found that these compositions are distinguished by a synergistic effect against acaridae and their eggs, and against insects.

The α-cyano-3-phenoxybenzyl-3-(2,2-dibromovinyl)-2,2-dimethyl-cyclopropane-carboxylate (German Pat. No. 2,326,077) is one of the interesting insecticides from the group of pyrethrinoids, especially the optically active steric configuration (S)-α-cyano-3-phenoxybenzyl-(1 R, 3 R)-3-(2,2-dibromovinyl)-2,2-dimethyl-cyclopropane-carboxylate (I, common name: Decamethrine) (German Offenlegungsschrift No. 24,39,177, see also Elliott et al., Nature 248,710,711 (1974)). However, Decamethrine has an insufficient activity against acaridae and their eggs.

The compounds II to VI are known plant protecting products. For example, II is described in German Pat. No. 1,015,797, and it is a commonly used insecticide in fruit and vegetable growing or in crop farming, such as in cotton, against biting and sucking insects, and in forestry against beetles, caterpillars and lice.

The compound III is known as well (see German Pat. No. 1,670,876), and used as insecticide and acaricide with a broad activity range against sucking and biting insects especially in cotton, fruits, vegetables, vine, cereals and rice.

The compounds IV (see German Pat. No. 1,099,787), V (see U.S. Pat. No. 3,264,177) and VI (see U.S. Pat. No. 2,812,280) are employed as acaricides in fruit and vegetable growing and other crop plants.

The compositions of the invention contain from 1 to 50 parts by weight of component I, and from 100 to 1 parts by weight of components II to VI, in combination with usual auxiliaries and carriers.

Suitable synergistic mixtures for combating insects are especially those of I with II or III, where the mixing ratio is from 1:1 to 1:100. The synergistic effect of these mixtures is particularly pronounced at a weight ratio (I:II and I:III, respectively) of 1:2.5 to 1:80, most preferably of 1:5 to 1:50. Combinations of I with III, IV, V or VI have an acaricidal effect; the weight ratio is these cases being in the range of from 1:2 to 50:1, preferably 1:1 to 50:1 and especially 3:1 to 30:1. Particularly advantageous are mixtures of I with IV or VI in a weight ratio of 1:1 to 30:1; of I with III in a weight ratio of 1:1 to 40:1; and of I with V in a weight ratio of 3:1 to 10:1.

The pesticides according to this invention, as compared to the individual component Decamethrine, have an improved action against insects living as parasites on crop plants or animals (Acarina) such as mesostigmata, for example dermanyssidae; metastigmata (ticks); prostigmata, for example trombiculidae, tetranychidae or panonychidae; astigmata or cryptostigmata. Because of their synergistic effect, they can be applied in considerably smaller amounts or lower concentration than the individual components for combating successfully the above pests.

In similar manner, using the insecticidal combinations of active substances, the insecticidal effects of the individual components are attained at a considerably lower concentration. Furthermore, the risk of resistance formation is thus reduced, which risk exists in all cases where a pest is combated by one single product for prolonged periods of time. Moreover, the compositions of the invention are even able to break a resistance already existing.

The combinations of the invention can be applied with success against important pests in numerous crop plants. For example, the combination I+II is especially suitable for combating Heliothis spp., Anthonomus spp. and Trichoplusia spp. in cotton, aphids in fruit and vegetable growing, caterpillars of butterflies in vegetable growing and caterpillars of vine moths in vine growing. The combination I+II can be applied with excellent results against caterpillars of butterflies, beetles such as Anthonomus spp. and aphids in cotton and citrus, in fruit, vegetable and vine growing and in crop farming.

The mixture of active substances according to the invention can be formulated in combination with solid or liquid inert carrier materials, adhesives, wetting agents, dispersing agents and grinding auxiliaries, in the form of wettable powders, emulsions, suspensions, dusts, granules or spreadable products. They can be mixed with other insecticides, fungicides, nematocides or herbicides.

Suitable solid carrier materials are mineral substances such as aluminum silicates, aluminum oxides, kaolin, chalks, siliceous chalks, talc, kieselguhr, or hydrated silicic acids or formulations of the aforesaid mineral substances with special additives, for example chalk treated with sodium stearate.

As liquid carrier materials, there may be used organic solvents such as ketones, for example methylethylketone, methylisobutylketone or isophorone, furthermore esters such as butyl acetate or glycol diacetate, ethers such as diethyleneglycoldimethyl ether, diethyleneglycoldiethyl ether or diethyleneglycoldibutyl ether, as well as high-boiling aromatics such as xylene, anisole, decalin or tetralin.

As adhesives, glue-like cellulose products or polyvinyl alcohols can be used.

Suitable wetting agents are all appropriate emulsifiers such as oxethylated alkylphenols, fatty alcohol-polyglycol ethers, fatty acid-polyglycol esters, salts of aryl- or alkylarylsulfonic acids, salts of methyltauride or soaps.

As dispersing agents there may be used cellulose waste liquors (salts of sulfite waste liquors), salts of naphthalene-sulfonic acid and in some cases also hydrated silicic acids or kieselguhr.

Suitable grinding auxiliaries are inorganic or organic salts such as sodium sulfate, ammonium sulfate, sodium carbonate, sodium bicarbonate, sodium thiosulfate, sodium stearate, or sodium acetate.

Depending on their formulation, the insecticidal and acaricidal compositions of the invention may contain from 2 to 90% of active substance, in combination with the above auxiliaries and carriers. Advantageously, they are used in the form of an emulsifiable concentrate containing from 10 to 70 weight % of the corresponding mixture of active substances, and from 5 to 15 weight % of a wetting agent, while the remainder consists up to 100 weight % of an organic solvent. Before application, this concentrate is diluted with a usual diluent, preferably water, to the intended concentration.

For the ultra-low-volume application process, in which highly concentrated mixtures are atomized via nozzles by flying airplanes, pesticides can be used which contain from 20 to 95 weight % of a mixture of active substances according to the invention, and from 80 to 5 weight % of aliphatic and/or aromatic mineral oils and/or ketones, each having a boiling point above 120° C., and/or vegetable oils such as cottonseed oil or castor oil, and/or liquid emulsifiers such as ethoxylated alkylphenols, for example nonylphenol, containing from 5 to 15 ethyleneoxide units per molecule.

The application concentration of the mixtures of active substances in the spraying liquors varies in dependence on the application mode and the climatic conditions, especially temperature and moisture. For spraying against acaridae and their eggs, for example, it may be in a range of from 0.005 to 0.05 weight %; a higher concentration, for example 0.1 weight %, being possible although generally not bringing about any technical advantage. Within the cited range, the concentration is nearer to the upper limit in the case of combinations containing larger amounts of I, while in the case of combinations containing smaller amounts of I, the concentration is nearer to the lower limit.

The following Examples illustrate the invention.

FORMULATION EXAMPLES

| 1. for combination products of Decamethrine (I) and Binapacryl (IV) | | | |
|---|---|---|---|
| | weight ratio I:IV | | |
| [Emulsion concentrates] | 1:1 | 4:1 | 10:1 |
| Decamethrine (ind. grade, 95%) | 2.53 | 2.53 | 2.53 |
| Binapacryl (ind. grade, 97%) | 2.53 | 0.63 | 0.25 |
| Calcium salt of dodecyl-benzenesulfonic acid (Phenylsulfonat Ca(R)) | 3.00 | 3.00 | 3.00 |
| Castor oil polyglycol ether (Emulsogen EL 360(R)) | 3.00 | 3.00 | 3.00 |
| Trisobutylphenolpolyglycol ether (Sapogenat T 110(R)) | 0.50 | 0.50 | 0.50 |
| Stabilizer (antioxidant) | 0.50 | 0.50 | 0.50 |
| Aromatic solvents (Solvesso 100(R)) | 87.94 | 89.84 | 90.22 |
| | 100.00 | 100.00 | 100.00 |

| 2. for combination products of Decamethrine (I) and Triazophos (III) | | | |
|---|---|---|---|
| | weight ratio I:III | | |
| [Emulsion concentrates] | 3:1 | 30:1 | 50:1 |
| Decamethrine (ind. grade, 95%) | 6.73 | 6.73 | 11.05 |
| Triazophos (ind. grade, 92%) | 2.16 | 0.23 | 0.23 |
| Calcium salt of dodecyl- | | | |

2. for combination products of Decamethrine (I) and Triazophos (III)

| [Emulsion concentrates] | weight ratio I:III | | |
|---|---|---|---|
| | 3:1 | 30:1 | 50:1 |
| benzenesulfonic acid (Phenylsulfonat Ca$^{(R)}$) | 8.50 | 8.00 | 7.50 |
| Castor oil polyglycol ether (Emulsogen EL 360$^{(R)}$) | 3.00 | 3.00 | 3.00 |
| Triisobutylphenolpolyglycol ether (Sapogenat T 110$^{(R)}$) | 1.00 | 1.50 | 2.00 |
| Epoxylated soybean oil (Kronos S$^{(R)}$) | 0.50 | 0.50 | 0.20 |
| Antioxidant | 0.50 | 0.50 | 0.80 |
| Xylene | 77.61 | 79.54 | 75.22 |
| | 100.00 | 100.00 | 100.00 |

3. for combination products of Decamethrine (I) and Cyhexatin (V)

| [Wettable powder] | weight ratio I:V = 8:1 |
|---|---|
| Decamethrine (ind. grade, 95%) | 8.40 |
| Cyhexatin (ind. grade, 90%) | 1.11 |
| Sodium salt of dinaphthyl-methanedisulfonic acid | 9.00 |
| Sodium salt of oleyl-N-methyltauride | 3.00 |
| Sodium salt of ligninsulfonic acid | 3.00 |
| Diatomaceous earth | 75.49 |
| | 100.00 |

4. for combination products of Decamethrine (I) and Dicofol (VI)

| (a) [Emulsion concentrate] | weight ratio I:VI = 4:1 |
|---|---|
| Decamethrine (ind. grade, 95%) | 4.20 |
| Dicofol (ind. grade, 90%) | 1.10 |
| Calcium salt of dodecylbenzenesulfonic acid (Phenylsulfonat Ca$^{(R)}$) | 5.50 |
| Castor oil polyglycol ether (Emulsogen EL 360$^{(R)}$) | 4.00 |
| Triisobutylphenolpolyglycol ether (Sapogenat T 300$^{(R)}$) | 1.80 |
| Antioxidant | 1.00 |
| Xylene | 82.40 |
| | 100.00 |

| (b) ULV-solution | |
|---|---|
| Decamethrine (ind. grade, 95%) | 4.20 |
| Dicofol (ind. grade, 90%) | 1.10 |
| High-boilingg aromatics (Solvesso 150$^{(R)}$) | 40.00 |
| Rapeseed oil | 54.70 |
| | 100.00 |

BIOLOGICAL EXAMPLES

Example 1

Larvae of the Mexican bean beetle (*Epilachna varivestis*) in the 3rd development stage, and the food thereof (*Phaseologis vulgaris*) were sprayed in the laboratory with equal amounts (dosage by machine) of active substances or mixtures thereof in differing concentration. Subsequently, the larvae so treated were placed on the dried leaves. The effect of the active substances or mixtures thereof was evaluated after 24 hours.

| | | concentration (%) of active substance | % mortality after 24 hours |
|---|---|---|---|
| (a) Mixing ratio 1:13 | | | |
| Compound | I | 0.000075 | 40 |
| " | II | 0.001 | 10 |
| " | I | 0.0000375 | 25 |
| " | II | 0.0005 | 0 |
| " | I | 0.0000375 | |
| + | | + | 65 |
| " | II | 0.0005 | |
| (b) Mixing ratio 1:65 | | | |
| Compound | I | 0.00009 | 38 |
| " | II | 0.00125 | 18 |
| " | I | 0.000015 | 21 |
| " | II | 0.001 | 15 |
| " | I | 0.000015 | |
| + | | + | 92 |
| " | II | 0.001 | |
| (c) Mixing ratio 1:2.7 | | | |
| Compound | I | 0.00009 | 37 |
| " | II | 0.00125 | 12 |
| " | I | 0.000075 | 30 |
| " | II | 0.0002 | 0 |
| " | I | 0.000075 | |
| + | | + | 83 |
| " | II | 0.0002 | |

Example 2

In the same manner as indicated in Example 1, combinations of the active substances I and III were tested for their activity against E. varivestis:

| | | Concentration (%) of active substance | % mortality after 24 hours |
|---|---|---|---|
| (a) Mixing ratio 1:16 | | | |
| Compound | I | 0.000075 | 40 |
| " | III | 0.0012 | 0 |
| " | I | 0.0000375 | 25 |
| " | III | 0.0006 | 5 |
| " | I | 0.0000375 | |
| + | | + | 65 |
| " | III | 0.0006 | |
| (b) Mixing ratio 1:80 | | | |
| Compound | I | 0.00001 | 48 |
| " | III | 0.0018 | 0 |
| " | I | 0.000019 | 16 |
| " | III | 0.0015 | 7 |
| " | I | 0.000019 | |
| + | | + | 97 |
| " | III | 0.0015 | |
| (c) mixing ratio 1:3.2 | | | |
| Compound | I | 0.0001 | 43 |
| " | III | 0.0018 | 0 |
| " | I | 0.000095 | 25 |
| " | III | 0.0003 | 0 |
| " | I | 0.000095 | |
| + | | + | 80 |
| " | III | 0.0003 | |

Examples 3 to 6

Combinations of the compounds I and III to VI were emulsified in water in such a manner that the concentrations of active substance as indicated in the following Tables were obtained. Subsequently, bean plants (*Phaseolus vulgaris*) heavily infested with a complete population (=all mobile and immobile stages including the eggs) of the red spider (*Tetranychus urticae*) were sprayed with these emulsions until beginning drip-off.

For a comparison, emulsions of the individual components were used in corresponding concentrations. After drying of the sprayed layers, the plants were placed in a greenhouse.

The results listed in the following Tables were obtained by microscopic control 8 days after the treatment.

Example 3

| | Combination I + III weight ratio: I:III = 30:1 | | |
|---|---|---|---|
| Active substance | wt. % AS in the spray liquor | Effect (% killing rate) acaricidal | ovicidal |
| mixture of I + III | I = 0.025 III = 0.00078 | — | 100 |
| I III | 0.025 0.00078 | — — | 50 25 |
| mixture of I + III | I = 0.0125 III = 0.00039 | — | 75 |
| I III | 0.0125 0.00039 | — — | 40 0 |
| mixture of I + III | I = 0.0063 III = 0.0002 | 90 | 45 |
| I III | 0.0063 0.0002 | 35 40 | 25 0 |
| mixture of I + III | I = 0.0031 III = 0.000098 | 80 | 0 |
| I III | 0.0031 0.000098 | 10 10 | 10 0 |
| mixture of I + III | I = 0.0016 III = 0.000048 | 35 | 30 |
| I III | 0.0016 0.000048 | 5 0 | 0 0 |

Example 4

| | Combination I + IV weight ratio: I:IV = 4:1 | | |
|---|---|---|---|
| Active substance | wt. % AS in the spray liquor | Effect (% killing rate) acaricidal | ovicidal |
| mixture of I + IV | I = 0.0063 IV = 0.0016 | 80 | 75 |
| I IV | 0.0063 0.0016 | 35 40 | 25 25 |
| mixture of I + IV | I = 0.0031 IV = 0.00078 | 50 | 40 |
| I IV | 0.0031 0.00078 | 10 20 | 10 10 |
| mixture of I + IV | I = 0.0016 IV = 0.00039 | 25 | 25 |
| I IV | 0.0016 0.00039 | 5 5 | 0 0 |

Example 5

| | Combination I + V weight ratio: I:V = 8:1 | |
|---|---|---|
| Active substance | wt. % AS in the spray liquor | Effect (% killing rate) ovicidal |
| mixture of I + V | I = 0.0125 V = 0.0016 | 80 |
| I V | 0.0125 0.0016 | 30 0 |
| mixture of I + V | I = 0.0063 V = 0.00078 | 50 |
| I V | 0.0063 0.00078 | 10 0 |

Example 6

| | Combination I + VI weight ratio: I:VI = 4:1 | | |
|---|---|---|---|
| Active substance | wt. % AS in the spray liquor | Effect (% killing rate) acaricidal | ovicidal |
| mixture of I + VI | I = 0.0125 VI = 0.0031 | — | 60 |
| I VI | 0.0125 0.0031 | — — | 30 0 |
| mixture of I + VI | I = 0.0063 VI = 0.0016 | 80 | 40 |
| I VI | 0.0063 0.0016 | 20 40 | 10 0 |
| mixture of II + VI | I = 0.0031 VI = 0.00078 | 50 | 20 |
| I VI | 0.0031 0.00078 | 15 10 | 0 0 |

What is claimed is:

1. An insecticidal and acaricidal composition containing a combination of compound I

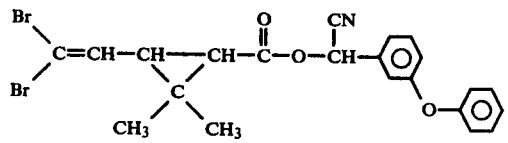

and compound III

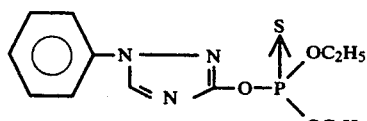

the weight ratio of compound I to compound III being 1:100 to 50:1.

2. An insecticidal composition which contains as its active ingredient a mixture of compound I

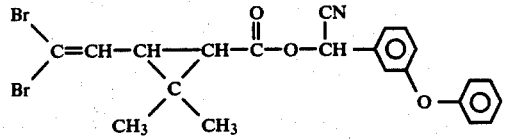

and compound III

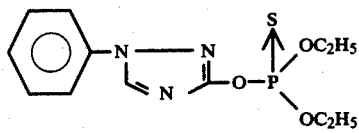

in a weight ratio of 1:1 to 1:100.

3. Insecticidal compositions as claimed in claim 2, wherein the active substances are present in a weight ratio of from 1:3.2 to 1:80.

4. An acaricidal composition which contains as its active ingredient a mixture of compound I

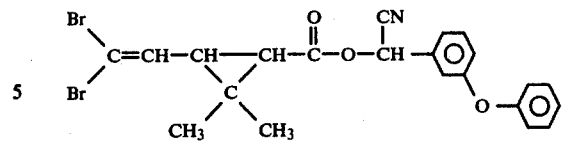

and compound III

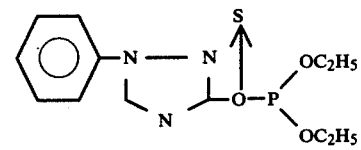

in a weight ratio of 1:1 to 50:1.

5. Acaricidal compositions as claimed in claim 4, wherein the weight ratio of the active substances is from 3:1 to 30:1.

6. A method of combating pests which comprises applying to the infested plants, soil, materials or animals an effective amount of a composition according to claim 2.

7. A method of combating pests which comprises applying to the infested plants, soil, materials or animals an effective amount of a composition according to claim 4.

* * * * *